United States Patent
Li et al.

(10) Patent No.: US 8,975,447 B2
(45) Date of Patent: Mar. 10, 2015

(54) PROCESS FOR ASYMETRIC METHYLALLYLATION IN THE PRESENCE OF A 2,2'-SUBSTITUTED 1,1'-BI-2-NAPHTHOL CATALYST

(75) Inventors: Wenjie Li, Hopewell Junction, NY (US); Zhi-Hui Lu, Newtown, CT (US); Chris Hugh Senanayake, Brookfield, CT (US); Yongda Zhang, Sandy Hook, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/003,248

(22) PCT Filed: Mar. 6, 2012

(86) PCT No.: PCT/US2012/027834
§ 371 (c)(1),
(2), (4) Date: Feb. 18, 2014

(87) PCT Pub. No.: WO2012/122152
PCT Pub. Date: Sep. 13, 2012

(65) Prior Publication Data
US 2014/0171692 A1   Jun. 19, 2014

Related U.S. Application Data

(60) Provisional application No. 61/449,742, filed on Mar. 7, 2011.

(51) Int. Cl.
| | |
|---|---|
| C07C 33/48 | (2006.01) |
| C07C 39/38 | (2006.01) |
| C07C 29/38 | (2006.01) |
| C07C 29/40 | (2006.01) |
| C07C 39/14 | (2006.01) |
| C07C 37/055 | (2006.01) |
| C07C 41/48 | (2006.01) |
| C07C 29/143 | (2006.01) |
| C07C 37/62 | (2006.01) |

(52) U.S. Cl.
CPC ............. *C07C 39/14* (2013.01); *C07C 29/38* (2013.01); *C07C 39/38* (2013.01); *C07C 37/055* (2013.01); *C07C 41/48* (2013.01); *C07C 29/143* (2013.01); *C07C 37/62* (2013.01); *C07B 2200/07* (2013.01)
USPC .......................................... 568/812; 568/719

(58) Field of Classification Search
None
See application file for complete search history.

(56) References Cited

U.S. PATENT DOCUMENTS 6,353,125 B1   3/2002   Wachtler et al.

FOREIGN PATENT DOCUMENTS

| WO | WO2010/011314 A1 * | 1/2010 | ........... C07D 413/10 |
|---|---|---|---|
| WO | 2011011123 A1 | 1/2011 | |

OTHER PUBLICATIONS

Morrison et al., Chemical Communications (2006), 27, pp. 2875-2877.*
Cox, P. et al., "Expidient Route to 3- and 3,3'-Substituted 1,1'-BI-2-Naphthols by Directed ortho Metalation and Suzuki Cross Coupling Methods." Tetrahedron Letters, 1992, vol. 33, No. 17, pp. 2253-2256.
International Search Report and Written Opinion for PCT/US2012/027834 mailed Aug. 1, 2012.
Orito, Y. et al., "Chiral base-catalyzed aldol reaction of trimethoxysilyl enol ethers: effect of water as an additive on stereoselectivities." Tetrahedron, 2006, vol. 62, No. 2-3, pp. 390-400.
Zou, Y. et al., "New diphosphite ligands for enantioselective asymmetric hydroformylation." Tetrahedron Letters, 2007, vol. 48, No. 27, pp. 4781-4784.

* cited by examiner

*Primary Examiner* — Brian J Davis
(74) *Attorney, Agent, or Firm* — Michael P. Morris; David L. Kershner

(57) ABSTRACT

Disclosed are a process and catalysts useful for carrying out asymmetric methlyallylations. The catalysts used in the invention have the formula (IV): wherein $X^1$, $X^2$, $R^3$ and $R^4$ are as defined herein. Compounds made by the process of the invention can be used to prepare pharmaceutically active compounds such as 11-β-hydroxysteroid hydrogenase type 1 (11-β-HSD1) inhibitors including 1,3-disubstituted oxazinan-2-ones.

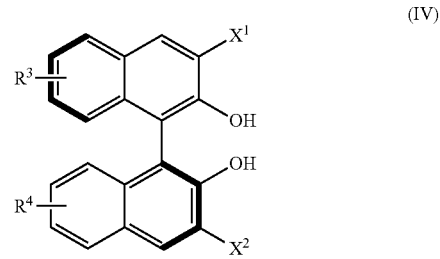

(IV)

15 Claims, No Drawings

PROCESS FOR ASYMETRIC METHYLALLYLATION IN THE PRESENCE OF A 2,2'-SUBSTITUTED 1,1'-BI-2-NAPHTHOL CATALYST

This application relates to a process and catalysts useful for carrying out asymmetric methlyallylations. Compounds made by the process of the invention can be used to prepare pharmaceutically active compounds such as 11-β-hydroxysteroid hydrogenase type 1 (11-β-HSD1) inhibitors, particularly 1,3-disubstituted oxazinan-2-ones.

BACKGROUND OF THE INVENTION 1,3-disubstituted derivatives of oxazinan-2-ones are reportedly useful as inhibitors of 11-β-hydroxysteroid hydrogenase type 1 ("11-β-HSD1") and for treatment of disorders associated with 11β-HSD1 activity including, for example, diabetes mellitus (e.g., type II diabetes), obesity, symptoms of metabolic syndrome, glucose intolerance, hyperglycemica (see, e.g., WO/2009/134400 and WO/2010/011314).

WO/2010/011314 describes several methods of making intermediates useful for making the 1,3-disubstituted oxazinan-2-ones. In one of the described methods, 1-chloro-3-phenylhex-5-en-3-ol is reacted with (S)-1-bromo-4-(1-isocyanatoethyl)benzene to form a mixture of diastereomers A and B as shown below.

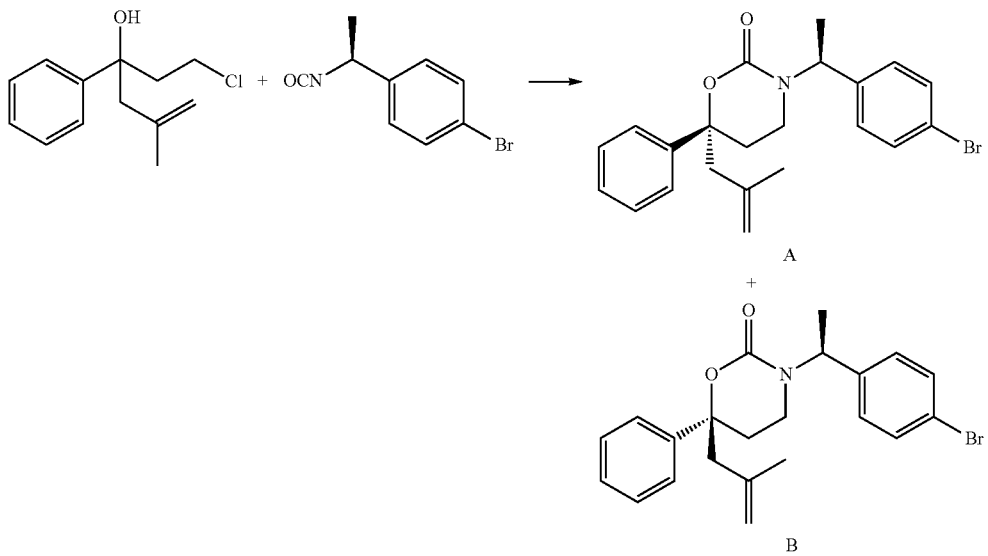

However, the isolated yield of the desired diastereomer (B) was only 34%. Moreover, the preparation of (S)-1-bromo-4-(1-isocyanatoethyl)benzene uses triphosgene, a highly toxic reagent. Thus, it is desirable to have a more efficient process making diastereomer B, for example, by preparing diastereomer B in higher yield and/or a more optically pure form.

BRIEF SUMMARY OF THE INVENTION

In its broadest embodiment, the subject application relates to processes for carrying out asymmetric methylallylations.

In one embodiment, the invention relates to a process for making compounds of formula (I) ("the process of the invention"):

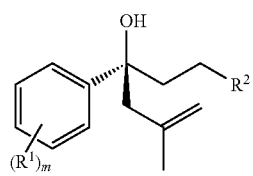

the process comprising allowing a compound of formula (II):

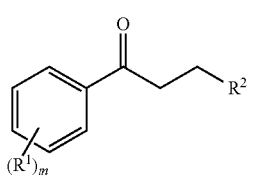

to react with a compound of formula (III):

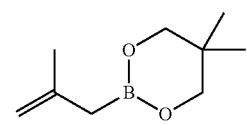

in the presence of a tertiary alcohol and a compound of formula (IV):

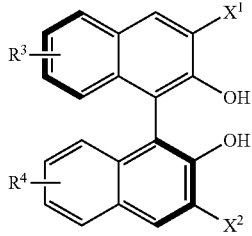

to provide the compound of formula (I):
wherein
m is 0, 1 or 2;
each $R^1$ is independently selected from —$(C_1$-$C_6)$alkyl, —$O(C_1$-$C_6)$alkyl, and —$(C_3$-$C_6)$cycloalkyl; wherein each of the —$(C_1$-$C_6)$alkyl, —$O(C_1$-$C_6)$alkyl, and —$(C_3$-$C_6)$cycloalkyl of said $R^1$ is optionally independently substituted with one to three groups selected from halo, —$(C_1$-$C_6)$alkyl, —$O(C_1$-$C_6)$alkyl, and —$(C_3$-$C_6)$cycloalkyl;
$R^2$ is a leaving group selected from chloro, bromo, iodo, methoxy, arylsulfonyloxy and trifluoromethanesulfonyloxy; and
$R^3$ and $R^4$ are each independently absent or a group selected from halo, —$(C_1$-$C_6)$alkyl, —$O(C_1$-$C_6)$alkyl, —$(C_3$-$C_6)$cycloalkyl, -(4- to 11-membered)heterocycloalkyl, —$(C_6$-$C_{10})$aryl, and -(5- to 11-membered)heteroaryl; and
$X^1$ and $X^2$ are each independently fluoro, chloro or bromo.

In another embodiment, the invention relates to the process of the invention wherein each $R^1$ is independently selected from —$(C_1$-$C_6)$alkyl, —$O(C_1$-$C_6)$alkyl, and —$(C_3$-$C_6)$cycloalkyl.

In another embodiment, the invention relates to the process of the invention wherein m is 0.

In another embodiment, the invention relates to the process of the invention wherein $R^2$ is selected from chloro, bromo, iodo.

In another embodiment, the invention relates to the process of the invention wherein $R^2$ is chloro.

In another embodiment, the invention relates to the process of the invention according to any of the embodiments above, wherein $X^1$ and $X^2$ are the same.

In another embodiment, the invention relates to the process of the invention according to the embodiment immediately above wherein $X^1$ and $X^2$ are each fluoro.

In another embodiment, the invention relates to the process of the invention according to the second embodiment immediately above wherein $X^1$ and $X^2$ are each chloro.

In another embodiment, the invention relates to the process of the invention according to the third embodiment immediately above wherein $X^1$ and $X^2$ are each bromo.

In another embodiment, the invention relates to the process of the invention according to the broadest embodiment above, wherein $X^1$ and $X^2$ are different.

In one embodiment, the invention relates to a process of the invention according to the broadest embodiment above, wherein m is 0; $R^2$ is selected from chloro or bromo; and $X^1$ and $X^2$ are each fluoro.

In another embodiment, the invention relates to a process of the invention according to the embodiment immediately above, wherein $R^2$ is chloro.

In another embodiment, the invention relates to a process of the invention according to the embodiment immediately above, wherein $R^3$ and $R^4$ are both absent.

In one embodiment, the invention relates to a process of the invention according to the broadest embodiment above, wherein m is 0; $R^2$ is selected from chloro or bromo; and $X^1$ and $X^2$ are each chloro.

In another embodiment, the invention relates to a process of the invention according to the embodiment immediately above, wherein $R^2$ is bromo.

In another embodiment, the invention relates to a process of the invention according to the embodiment immediately above, wherein $R^3$ and $R^4$ are both absent.

In one embodiment, the invention relates to a process of the invention according to the broadest embodiment above, wherein m is 0; $R^2$ is selected from chloro or bromo; and $X^1$ and $X^2$ are each bromo.

In another embodiment, the invention relates to a process of the invention according to the embodiment immediately above, wherein $R^2$ is chloro.

In another embodiment, the invention relates to a process of the invention according to the embodiment immediately above, wherein $R^3$ and $R^4$ are both absent.

In another embodiment, the invention relates to a process of the invention according to the broadest embodiment above, wherein at least one of $R^3$ and $R^4$ is halo.

In another embodiment, the invention relates to a process of the invention according to the broadest embodiment above, wherein at least one of $R^3$ and $R^4$ is —$(C_1$-$C_6)$alkyl.

In another embodiment, the invention relates to a process of the invention according to any of the embodiment above, wherein the tertiary alcohol is t-amyl alcohol or t-butyl alcohol.

In another embodiment, the invention relates to a process of the invention according to the embodiment immediately above, wherein the tertiary alcohol is t-amyl alcohol.

In another embodiment, the invention relates to a process of the invention according to the second embodiment immediately above, wherein the tertiary alcohol is t-butyl alcohol.

In another embodiment, the invention relates to a compound of formula (IVa):

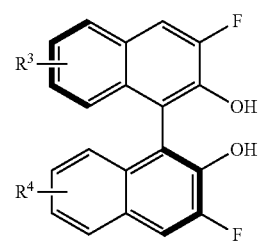

wherein $R^3$ and $R^4$ are as defined above.

In another embodiment, the invention relates to a compound of formula (IVa), wherein at least one of $R^3$ and $R^4$ is a group selected from halo, —$(C_1$-$C_6)$alkyl, —$O(C_1$-$C_6)$alkyl, —$(C_3$-$C_6)$cycloalkyl, -(4- to 11-membered)heterocycloalkyl, —$(C_6$-$C_{10})$aryl, and -(5- to 11-membered)heteroaryl.

In another embodiment, the invention relates to a compound of formula (IVa), wherein at least one of $R^3$ and $R^4$ is halo.

In another embodiment, the invention relates to a compound of formula (IVa), wherein at least one of $R^3$ and $R^4$ is —$(C_1$-$C_6)$alkyl.

In a particular embodiment, the invention relates to a compound of formula (IVa) wherein $R^3$ and $R^4$ are each absent. Such compound is named (S)-3,3'-difluoro-1,1'-binaphthyl-2,2'-diol and has the structure (3):

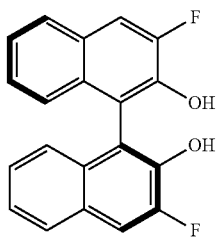

The invention still further relates to a method of making the compound of formula (IV). In one embodiment, the method comprises allowing a compound of formula (IV-3):

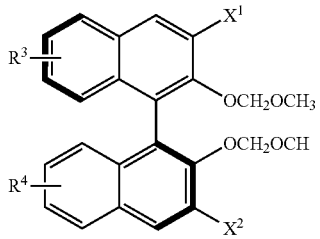

to react with a proton source to provide the compound of formula (IV).

In another embodiment, the invention relates to the embodiment immediately above further comprising the step of allowing of a compound of formula (IV-2):

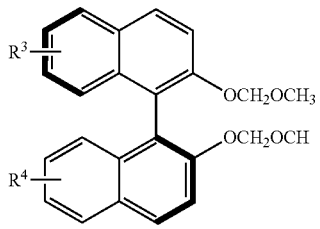

to react with a lithium alkyl followed by reaction with a halide source to provide the compound of formula (IV-3).

In another embodiment, the invention relates to any of the two embodiments immediately above, wherein $X^1$ and $X^2$ are each fluoro.

In another embodiment, the invention relates to the second and third embodiments immediately above, wherein $X^1$ and $X^2$ are each chloro.

In another embodiment, the invention relates to the third and fourth embodiments immediately above, wherein $X^1$ and $X^2$ are each bromo.

In another embodiment, the invention relates to any of the three embodiments immediately above, wherein $R^3$ and $R^4$ are both absent.

DETAILED DESCRIPTION OF THE INVENTION

Abbreviations (S)-DBBINOL=(S)-3,3'-dibromo-1,1'-binaphthyl-2,2'-diol (also referred to as compound 1)
(S)-DCBINOL=(S)-3,3'-dichloro-1,1'-binaphthyl-2,2'-diol (also referred to as compound 2)
(S)-DFBINOL=(S)-3,3'-difluor-1,1'-binaphthyl-2,2'-diol (also referred to as compound 3)
Di-halo-naphthyl-diol catalyst=compound of formula (IV)
n-BuLi=n-butyl lithium
DIBAL-H=diisobutylaluminum hydride
EtOAc=ethyl acetate
$Et_2O$=diethyl ether
LiHMDS=lithium hexamethyldisilazide
MeOH=methanol
MMPP=magnesium bis(monoperoxyphtalate) hexahydrate
MOMCl=chloro(methoxy)methane
MTBE=methyl tert-butyl ether
NFSI=N-fluoro-N-(phenylsulfonyl)benzenesulfonamide
t-BuOH=tert-butanol or t-butanol
THF=tetrahydrofuran The term "$(C_1-C_6)$alkyl" refers to branched and unbranched alkyl groups having from 1 to 6 carbon atoms. Examples of —$(C_1-C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the $(C_1-C_6)$alkyl group can be the point of attachment to another group or moiety.

The term "$(C_3-C_6)$cycloalkyl" refers to a nonaromatic 3- to 6-membered monocyclic carbocyclic radical. Examples of "$(C_3-C_6)$cycloalkyls" include cyclopropyl, cyclobutyl, cyclohexyl, cyclopentyl and cyclohexyl.

As used herein, the term "$(C_6-C_{10})$aryl" refers to an aromatic hydrocarbon rings containing from six to ten carbon ring and includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "4 to 11-membered heterocycle" includes stable nonaromatic 4-8 membered monocyclic heterocyclic radical or a stable nonaromatic 6 to 11-membered fused bicyclic, bridged bicyclic or spirocyclic heterocyclic radical. The 4 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

As used herein, the term "5 to 11-membered heteroaryl" includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl.

It will be understood that when a heterocyclyl or heteroaryl contains a S ring atom, such S ring atom can be present in the ring in its divalent, tetravalent, or hexavalent form, i.e., —S—, —S(O)— or —S(O)$_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "heteroatom" as used herein shall be understood to mean atoms other than carbon such as O, N, and S.

The term "halo" or "halogen" refers to fluoro, chloro, bromo or iodo.

As discussed above, the subject invention relates, in one embodiment, to a process for carrying out asymmetric methlyallylations. The process of the invention is depicted in Scheme 1 below:

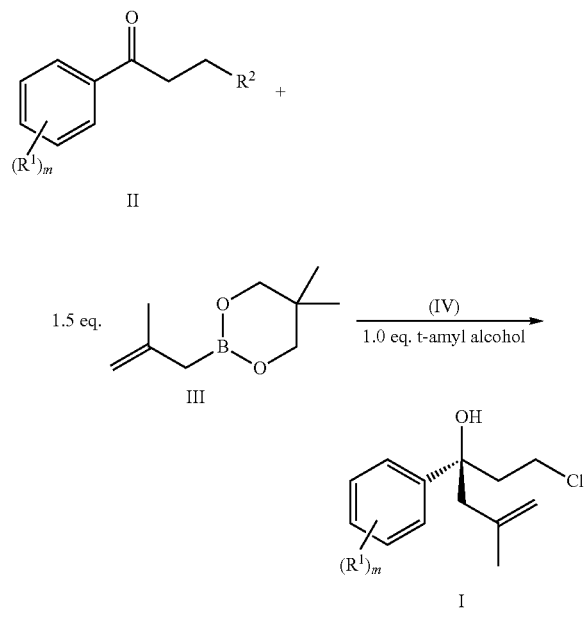

As depicted in Scheme 1, a compound of formula II is allowed to react with 5,5-dimethyl-2-(2-methylallyl)-1,3,2-dioxaborinane (III) in the presence of a compound of formula (IV) (i.e., a di-halo-naphthyl-diol catalyst) in a tertiary alcohol solvent (e.g., t-amyl alcohol or t-butanol) to provide the compound of formula (I). The reaction can be carried out at a temperature of from about the melting point of the tertiary alcohol solvent up to about the boiling point of the tertiary alcohol solvent. In one embodiment the reaction is carried out a temperature of from about 10° C. to about 100° C.; in another embodiment, from about 20° C. to about 70° C.; and in another embodiment, from about 23° C. up to 60° C. The reaction is typically carried out with a slight excess of the compound of formula (III), e.g., a 1.5 molar equivalents per molar equivalent of the compound of formula (II). Thus, the reaction is typically carried for a time sufficient to allow substantially all of the compound of formula (II) to react with the compound of formula (III). The optimum reaction time will depend on factors such as the substituent groups $R^1$, the relative amount of the compound of formula (III), the tertiary alcohol solvent, and the di-halo-naphthyl-diol. Reaction time can be from about 1 hour up to about 30 hours. Applicants have found that the reaction time is strongly dependent on the relative amount of the compound of formula (IV). In some embodiments, when a sufficient amount of the compound of formula (IV) is present, the reaction time is less than 1 hour. The reaction is typically carried out using anhydrous reagents and under inert atmosphere (e.g., $N_2$, He or Ar). The process of the invention is used to prepare the compound of formula (I) depicted above in high yield and substantially free of its optical isomer (not shown). According to the process of the invention, the compound of formula (I) as depicted herein is provided in an amount of at least about 85 mol %, more preferably at least about 90 mol %, even more preferably at least about 95 mol %, most preferably at least about 98 mol % based on the total amount of the compound of formula (I) and its optical isomer (not shown). If desired, the compound of formula (I) can be isolated by quenching with aqueous acid, optionally in the presence of added toluene. The resultant organic phase is then collected and washed with aqueous caustic to remove the compound of formula (IV) followed by sufficient amount of water to achieve a pH of about 8.5. The organic phase can then be concentrated and used without further purification. If desired, the compound of formula (IV) can be recovered from the aqueous caustic wash by acidifying it with aqueous acid. The compound of formula (IV) precipitates from the acidified wash and can be collected and reused for additional asymmetric methylallylation.

Compounds of formula (II) are commercially available or can be prepared by known methods. The compound of formula (III) can be prepared by the method described in the Examples section.

The compound of formula (IV) (di-halo-naphthyl-diol catalyst) can be prepared by known methods (see, e.g., *J. Org. Chem.* 2000, 65, 6319; and *Letters in Organic Chemistry*, 2006, 3, 735), by the methods described herein in the Examples section for the preparation of compound 3, and the method depicted below in Scheme 2.

Scheme 2

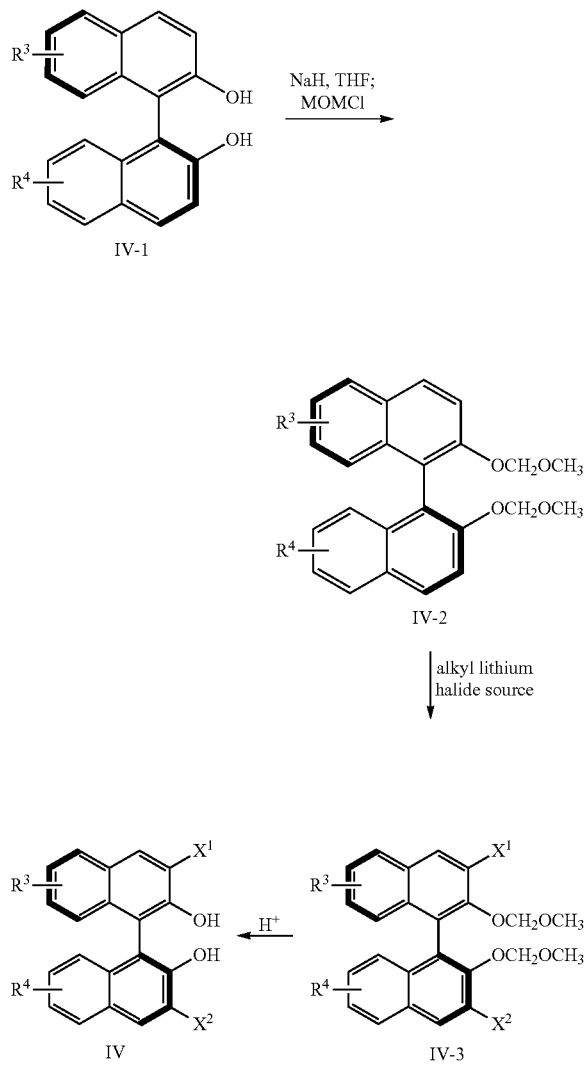

As depicted in Scheme 2, a compound of formula (IV-1) is allowed to react with chloro(methoxy)methane (MOMCl) to provide a compound of formula (IV-2). The compound of formula (IV-2) is then allowed to react with an alkyl lithium reagent (e.g., BuLi) followed by reaction with a halide source to provide the compound of formula (IV-3). Nonlimiting examples of halide sources include, e.g., N-fluoro-N-(phenylsulfonyl)benzenesulfonamide (NFSI) and N-fluoro-o-benzenedisulfonimide (NFOBS) for fluoride; hexachloroethane for chloro; and $Br^2$ or 1,1-1,2-tetrabromoethane for bromo. The compound of formula (IV-3) is then allowed to react with a proton source (e.g., Amberlyst® resins sold by Rohm and Haas and available from Sigma-Aldrich) to provide the compound of formula (IV). Compounds of formula (IV-1) can be prepared by known methods (see, e.g., *Journal of Organic Chemistry* 60: 7388-9 (1995); *Journal of the Chemical Society, Perkin Transactions 1: Organic and Bio-Organic Chemistry* 2097-2104 (1998); and *Journal of Organic Chemistry* 68:7921-7924 (2003)).

As noted above, compounds of formula (I) prepared by the process of the invention are useful for making pharmaceutically active compounds such as 11-β-hydroxysteroid hydrogenase type 1 (11-β-HSD1) inhibitors, particularly, oxazinan-2-one 11-β-HSD1 inhibitors which are described in WO/2009/134400 and WO/2010/010150. Scheme 3 below depicts a method of making the oxazinan-2-one 11-β-HSD1 inhibitors using the compound of formula (I) prepared according to the process of the invention.

Scheme 3

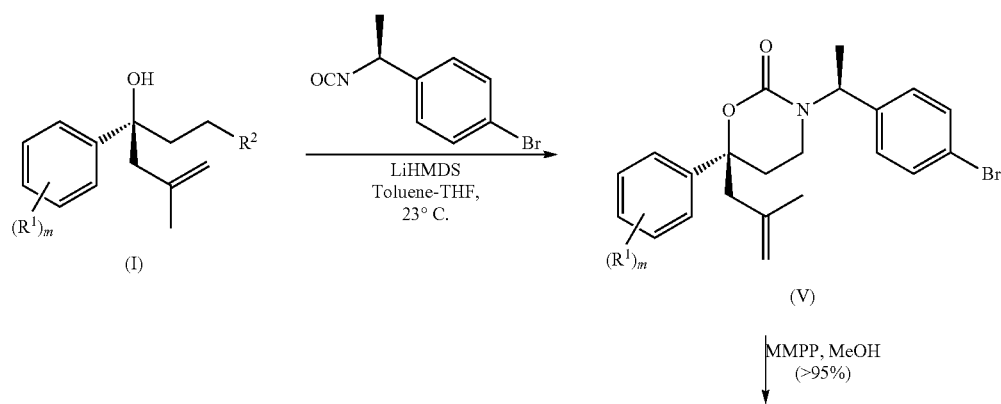

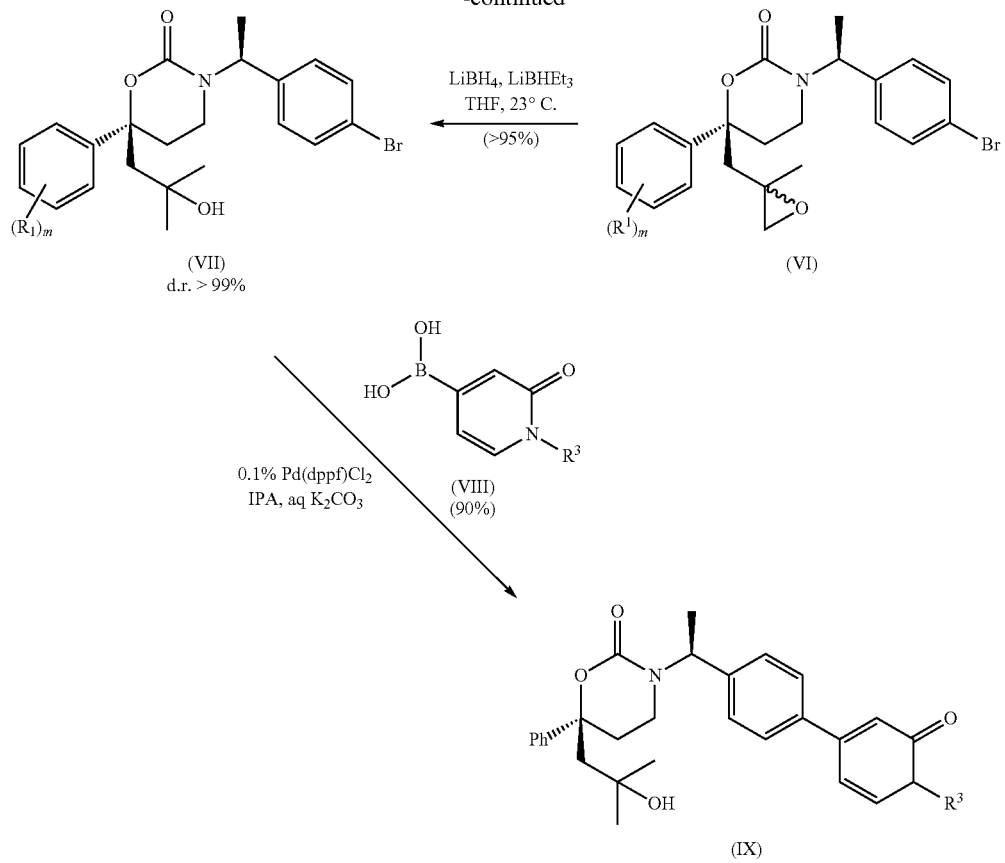

For the compounds depicted in Scheme 3, $R^1$, $R^2$ and m are as defined above; and $R^3$ is selected from —$(C_1$-$C_6)$alkyl and —$(C_3$-$C_6)$cycloalkyl.

As depicted in Scheme 3, the compound of formula (I) is allowed to react with (S)-1-bromo-4-(1-isocyanatoethyl)benzene in the presence of LiHMDS in a toluene-THF solvent to provide the compound of formula (V) in 95% yield and substantially free of its diastereomers. The compound of formula (V) is then allowed to react with MMPP in methanol to provide the compound of formula (VI) which is then reacted with LiBH$_4$ and LiBHEt$_3$ to provide the compound of formula (VII). The compound of formula (VII) is then allowed to react with the compound of formula (VIII) in the presence of a palladium catalyst to provide the compound of formula (IX). The preparation of (S)-1-bromo-4-(1-isocyanatoethyl)benzene and the compound of formula (VIII) are described in WO/2010/011314. By using a more optically form of the compound of formula (I), the compound of formula (V) can be prepared in higher yield and in purer form than methods described in WO/2010/011314.

In one embodiment, the invention relates to a method of making the compound of formula (V), the process comprising allowing a compound of formula (I) to react with (S)-1-bromo-4-(1-isocyanatoethyl)benzene in the presence of LiHMDS to provide the compound of formula (V), wherein the compound of formula (I) is prepared by any of the embodiments described above.

In another embodiment, the invention relates to the embodiment immediately above wherein the compound of formula (I) used to prepared the compound of formula (V) is present in an amount of at least about 85 mol %, more preferably at least about 90 mol %, even more preferably at least about 95 mol %, most preferably at least about 98 mol % based on the total amount of the compound of formula (I) and its optical isomer.

In another embodiment, the invention relates to a method of making the compound of formula (IX), the process comprising (i) allowing a compound of formula (V) to react with MMPP in methanol to provide the compound of formula (VI);

(ii) allowing the compound of formula (VI) formed in Step (i) to react with LiBH$_4$ and LiBHEt$_3$ to provide the compound of formula (VII); and (iii) allowing the compound of formula (VII) formed in Step (ii) to react with the compound of formula (VIII) in the presence of a palladium catalyst to provide the compound of formula (IX); wherein the compound of formula (V) used in Step (i) is prepared according either of the tow embodiments described immediately above.

In another embodiment, the invention relates to a method of making the compound of formula (IX) according to any of the embodiments above, wherein m is 0, and $R^3$ is methyl or cyclopropyl.

In another embodiment, the invention relates to a method of making the compound of formula (IX) as according to the embodiment immediately above, wherein $R^3$ is cyclopropyl.

In another embodiment, the invention relates to a method of making the compound of formula (IX) according to the second embodiment immediately above, wherein $R^3$ is methyl.

EXAMPLES

General Procedures

The purity of the compounds described in the Examples section is determined using high performance liquid chromatography (HPLC) and nuclear magnetic resonance (NMR) spectroscopy. Reverse phase HPLC is used to determine the amount of each diastereomer present and the ratio of these amounts is used to determine the chiral purity of the diastereomeric product.

[1]NMR spectra are recorded on a 400 MHz Bruker spectrometer using d-6 DMSO as the sample solvent.

Example 1

Preparation of (S)-3,3'-difluoro-1,1'-binaphthyl-2,2'-diol (3)

Step 1: Synthesis of (S)-2,2'-bis(methoxymethoxy)-1,1'-binaphthyl (4)

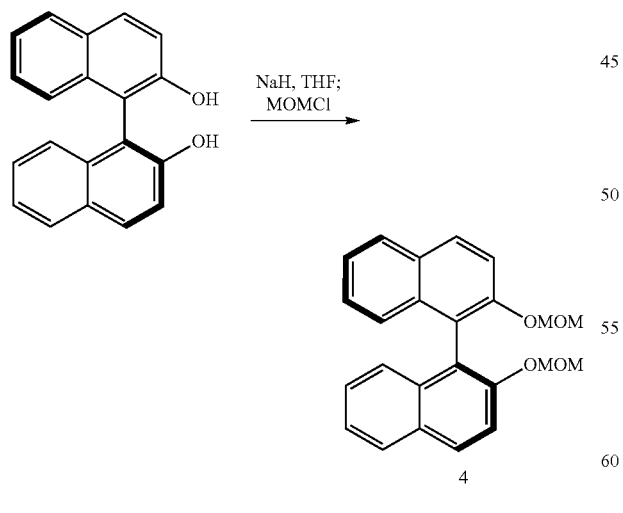

A solution of (R)-1,1'-binaphthyl-2,2'-diol (30 g, 0.10 mol) in THF (200 ml) is added to a stirred slurry of 60 wt % NaH (10.48 g, 0.26 mol) in THF (100 mL) at 0-10° C. The mixture is stirred 1 hour and treated with chloro(methoxy)methane (MOMCl) (20.25 g, 0.25 mol) while maintaining the temperature below 10° C. The resultant mixture is stirred for 1 hour at 0-5° C. then treated with water (100 mL) to quench the reaction. The organic phase is collected and the aqueous phase extracted with EtOAc (2×250 mL). The combined organics layers are washed with water (200 mL) and concentrated. The resultant pale yellow solid is then slurried in 10:1 (vol/vol) hexane/EtOAc. The solids are collected by filtration and dried under reduced pressure to provide 4 as a white solid. Yield: 38.5 g, 98%.

Step 2: Synthesis of (S)-3,3'-difluoro-2,2'-bis(methoxymethoxy)-1,1'-binaphthyl (5)

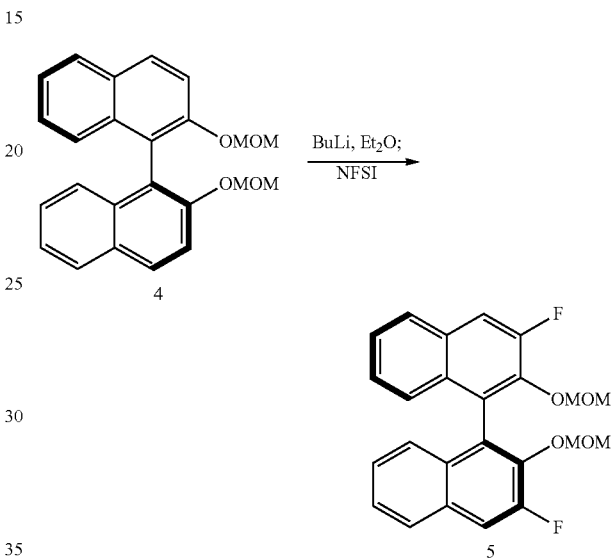

A solution of n-BuLi (1.6M, 30.46 mL, 48.7 mL) in hexane is added to a stirred solution of 4 in Et₂O (400 mL). After 3 hours the resultant slurry is cooled to 0° C., treated with THF (40 mL), mixed for 0.5 hour, and treated with a solution of N-fluoro-N-(phenylsulfonyl)benzenesulfonamide (NFSI) (15.5 g, 49.2 mmol) in THF (40 mL). After 10 minutes the reaction is quenched with water, and the organic layer is collected. The aqueous layer is extracted with EtOAc (2×100 mL), and the combined organic layer is washed with water (100 mL) and concentrated. The resultant residue is redissolved in a minimum volume of toluene, added to a silica gel column, eluted with hexane/EtOAc, and concentrated to provide 5 as a white solid. Yield: 6.3 g, 77%.

Step 3: Synthesis (S)-3,3'-difluoro-1,1'-binaphthyl-2,2'-diol (3)

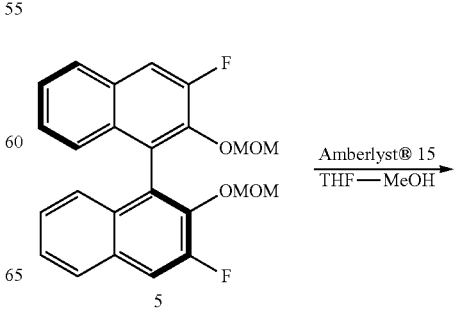

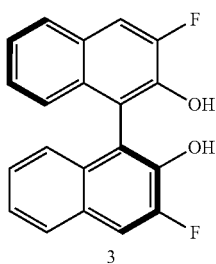

Amberlyst® 15 (Aldrich) (6 g) is added to a stirred solution of 5 (5.6 g, 13.7 mmol) in 1:1 THF/MeOH (vol/vol) (60 mL). The resultant mixture is heated at reflux for 3 hours then allowed to cool to about 25° C. The mixture is then filtered through a Celite pad, and the filtrate is concentrated. The resultant residue is redissolved in a minimum volume of toluene, added to a silica gel column, eluted with hexane/EtOAc, and concentrated to provide 3 as a white solid. Yield: 4.3 g, 97%. $^1$H NMR (500 MHz, CDCl$_3$): δ 7.79 (d, 2H, J=8.2 Hz), 7.65 (d, 2H, J=11.2 Hz), 7.36 (t, 2H, J=7.4 Hz), 7.22 (t, 2H, J=7.9 Hz), 7.10 (d, 2H, J=8.5 Hz), 5.96 (s, 2H). MS: 323 (M+H).

Example 2

Synthesis of 5,5-dimethyl-2-(2-methylallyl)-1,3,2-dioxaborinane (6)

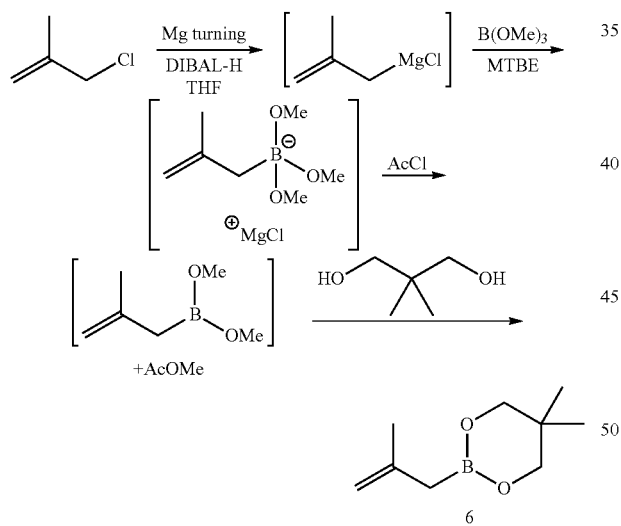

A reactor is purged with N$_2$ and charged with magnesium turnings (29.16 g, 1.21 mol) and dry THF (1 liter). The contents of the reactor are maintained at 20-25° C. and treated with a 1 M solution of DIBAL-H in heptane (33.1 mL of solution; 0.03 mol of DIBAL-H) followed by slow addition of 3-chloro-2-methyl-1-propene (100.0 g; 1.10 mol). The resultant mixture is maintained at 20-25° C. for 2 hours and filtered to provide the Grignard reagent. (Typical yield of Grignard reagent is 85%.) The resultant filtrate is treated with methyl-t-butyl ether (370.0 g, 4.2 mol), cooled to −65° C., and treated with trimethylboronate (80.0 g, 0.77 mol) while maintaining a temperature of less than −60° C. The resultant milky solution is maintained at −55 to −60° C. for 30 minutes and slowly warmed to 0° C. over 30 minutes. The mixture is then treated with acetyl chloride (54.4 g, 0.69 mol) while maintaining a temperature of less than 5° C. The mixture is allowed to slowly warm to about 20° C. over 30 minutes and treated with a solution of 2,2-dimethyl-1,3-propanediol (72.2 g, 0.69 mol) in THF (144 mL). The reaction mixture is maintained at about 20° C. for 6 hours, concentrated to about ⅓ of its original volume under reduced pressure at a temperature of less than about 29° C., and treated with MTBE (360 mL) and heptane (720 ml). The resultant mixture is again reduced to about ⅓ of its original volume under reduced pressure, filtered through Celite, and the Celite plug rinsed with MTBE (2.165 L). The combined filtrates are then concentrated under reduced pressure at 29° C. to provide 6 as a colorless oil. Yield: 93.16 g; 75% based on 2,2-dimethyl-1,3-propanediol. Compound 6 is further purified by vacuum distillation prior to use in Example 3.

Example 3

Compounds 1, 2 and 3 can be used to carry out the asymmetric methylallylation as depicted below:

Di-halo-naphthyl-diol catalyst

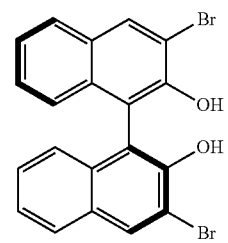

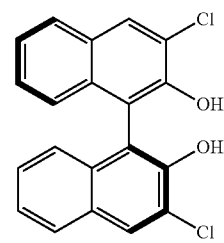

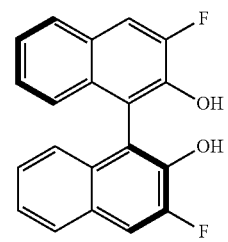

Asymmetric methylallylation using the compounds of formula 1, 2, or 3

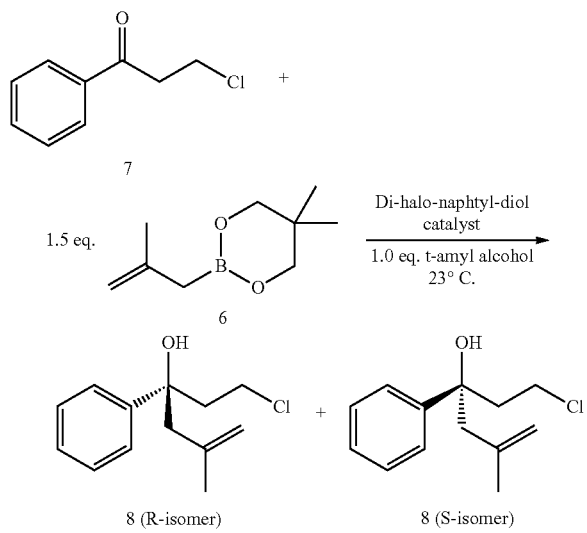

General procedure for the catalytic asymmetric methylallylation using compound 3 to prepare (R)-1-chloro-5-methyl-3-phenylhex-5-en-3-ol (8): A $N_2$-filled flask is charged with 3-chloro-1-phenyl-butan-1-one (7) (10 g, 58 mmol), t-amyl alcohol (5.12 g, 58.11 mmol), and compound 3 (0.56 g, 1.7 mmol). The reaction mixture is maintained at a temperature of about 23° C. and treated with 6 (14.51 g, 81.4 mmol) and stirred for about 22-24 hours. Samples of the reaction mixture are removed periodically and the reaction progress monitored using HPLC or infrared spectroscopy. (See Ex 3d in the Table below.) After 24 hours compound 8 is present in 88% yield. The selectivity is about 88:12 favoring the R-isomer (determined by the HPLC method described below). Compound 8 is isolated from the reaction mixture by treating the mixture with water (50 mL), hexanes (50 mL), 3M HCl (1 mL), and stirring for 1 hour. The resultant organic layer is collected and washed with water (20 mL), 1M NaOH (2×10 mL), and water (2×10 mL). The organic layer is then concentrated to provide a mixture of 8 (R- and S-isomers) as a pale yellow oil. Yield: 13 g, 13.0 mmol. The mixture of isomers is typically used in the next reaction step without further purification.

HPLC method:
Column: Chiralcel OJ-RH
Flow rate: 1.3 mL/min; Col. Temp: 25 C
MP A: water with ammonium formate pH=4; MP C: acetonitrile The above reaction is also carried out using the dibromo analog (1) and dichoro analog (2) of compound 3. The catalytic performances of all the three catalysts are shown in the Table 1 below including the % conversion and the isomer ratios (R-isomer:S-isomer).

TABLE 1

Effect of catalyst and catalyst concentration on % conversion and isomer ratio (R-isomer:S-isomer).

| Ex. | Catalyst (mol %) | 4 h | 7 h | 22 h | 30 h |
|---|---|---|---|---|---|
| 3a | 1 (20 mol %) | 48% (93:7) | 69% (93:7) | 83% (93:7) | — |
| 3b | 2 (17 mol %) | 78% (93:7) | 89% (93:7) | 98% (93:7) | — |
| 3c | 2 (5 mol %) | 39% (90:10) | — | 86% (90:10) | 90.4% (90:10) |

TABLE 1-continued

Effect of catalyst and catalyst concentration on % conversion and isomer ratio (R-isomer:S-isomer).

| Ex. | Catalyst (mol %) | 4 h | 7 h | 22 h | 30 h |
|---|---|---|---|---|---|
| 3d | 3 (1 mol %) | 25% (7.5 h) | 40% (23 h) | 78% | 84% (29 h) (87:13) |
| 3e | 3 (3 mol %) | 51%, | 71% (8 h) | 99.8% 87.6:12.4 | — |
| 3f | 3 (6 mol %) | 77.5% | 97.4% (8 h) | 100% (87.7:12.3) | |
| 3g | 3 (9 mol %) | 91.5% | 99.7% (6 h) (88:12) | | |

Example 4

Example 4 describes the effect of temperature and catalyst concentration on rate and yield of the asymmetric methylallylation described in Example 3. The results are shown in Table 2 below:

TABLE 2

Effect of temperature and catalyst concentration on % conversion and isomer ratio (R-isomer:S-isomer).

| Ex. | Temp., ° C. | Catalyst (mol %) | 6 h | 9 h | 22-23 h |
|---|---|---|---|---|---|
| 4a | 30 | 3 (1 mol %) | 46% (84.3:15.7) | — | 93% (83:17) |
| 4b | 40 | 3 (1 mol %) | 57% (85.2:14.8) | — | 98.2% (85.5:14.5) |
| 4c | 50 | 3 (1 mol %) | 65% (84.1:15.9) | — | 99.5% (84.8:15.2) |
| 4d | 60 | 3 (1 mol %) | 71% (82.7:17.3) | — | 99.2% (82.6:17.4) |
| 4e | 30 | 3 (2 mol %) | 70% (87.1:12.9) | — | 99.4% (86:14) |
| 4f | 40 | 3 (2 mol %) | 79.5% (86.6:13.4) | — | 99.7% (86.5:13.5) |
| 4g | 50 | 3 (2 mol %) | 80.5% (85.2:14.8) | — | 95% (85.2:14.8) |
| 4h | 60 | 3 (2 mol %) | 73.2% (84.2:15.8) | — | 79% (82.8:17.2) |
| 4i | 30 | 3 (3 mol %) | 86% (87:13) | 98.2% (87:1) | — |
| 4j | 40 | 3 (3 mol %) | 94.3% (87:13) | 99% (86:14) | — |
| 4k | 50 | 3 (3 mol %) | 97.2% (85:15) | 98.9% (86:14) | — |
| 4l | 60 | 3 (3 mol %) | 97.2% (85:15) | 100% (86:14) | — |
| 4m | 30 | 2 (5 mol %) | 46% (92.7:7.3) | — | 67% (92:8) |
| 4n | 40 | 2 (5 mol %) | 51% (91:9) | — | 57% (88.8:11.2) |
| 4o | 50 | 2 (5 mol %) | 36% (88:12) | — | 38% (86:14) |
| 4p | 60 | 2 (5 mol %) | 31.4% (85:15) | — | 32% (83:17) |

The results in Table 2 show that for catalyst 3, increased reaction temperature over the range from 30° C. to 60° C. increases the rate of conversion without significantly affecting the ratio of R-isomer:S-isomer. Conversely, increasing the temperature from 30° C. to 60° C. for catalyst 2 decreases the rate and extent of product formation along with the ratio of R-isomer:S-isomer.

Example 5

Example 5 describes the effect of the amount and type of alcohol on the rate and yield of the asymmetric methylallylation described in Example 3 using catalyst 3 at 40° C. The results are shown in Table 3 below. In Examples 5a-5d, 1.5 equivalents of dioxaborinane (compound 6) are used. In Examples 5e-5h, 1.5 equivalents of compound 6 are used.

TABLE 3

Effect of alcohol on % conversion and isomer ratio (R-isomer:S-isomer).

| Ex. | Alcohol | 2.5 h | 15 h | 17.5 h |
|---|---|---|---|---|
| 5a | 1.0 eq. t-amyl alcohol | — | 98% (87:13) | — |
| 5b | 2.0 eq. t-amyl alcohol | — | 99.4% (87:13) | — |
| 5c | 3.0 eq. t-amyl alcohol | — | 98% (87:13) | — |
| 5d | 1.0 eq. t-butyl alcohol | — | 98% (87:13) | — |
| 5e | 1.0 eq. t-butyl alcohol | 65% (87:13) | — | 100% (87:13) |
| 5f | 2.0 eq. t-butyl alcohol | 64% (87:13) | — | 100% (87:13) |
| 5g | 3.0 eq. t-butyl alcohol | 55% (87:13) | — | 97.4% (87:13) |
| 5h | 1.0 eq. i-propanol | 7% (80:20) | — | 35% (76:24) |

The results in Table 3 show that tertiary alcohols (t-amyl alcohol and t-butyl alcohol) provide higher yield of product and a higher R-isomer:S-isomer ratio than the less sterically hindered isopropanol.

What is claimed is:

1. A process for making a compound of formula (I):

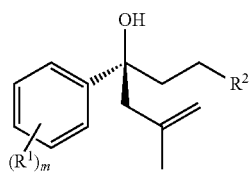

I the process comprising allowing a compound of formula (II):

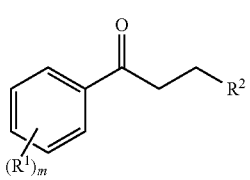

II to react with a compound of formula (III):

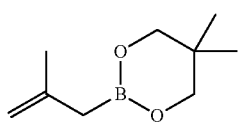

III in the presence of a tertiary alcohol and a compound of formula (IV):

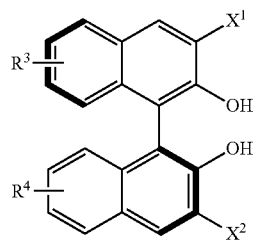

IV to provide the compound of formula (I):
wherein
m is 0, 1 or 2;
each $R^1$ is independently selected from —$(C_1$-$C_6)$alkyl, —$O(C_1$-$C_6)$alkyl, and —$(C_3$-$C_6)$cycloalkyl; wherein each of the —$(C_1$-$C_6)$alkyl, —$O(C_1$-$C_6)$alkyl, and —$(C_3$-$C_6)$cycloalkyl of said $R^1$ is optionally independently substituted with one to three groups selected from halo, —$(C_1$-$C_6)$alkyl, —$O(C_1$-$C_6)$alkyl, and —$(C_3$-$C_6)$cycloalkyl;
$R^2$ is a leaving group selected from chloro, bromo, iodo, methoxy, arylsulfonyloxy and trifluoromethanesulfonyloxy; and
$R^3$ and $R^4$ are each independently absent or a group selected from halo, —$(C_1$-$C_6)$alkyl, —$O(C_1$-$C_6)$alkyl, —$(C_3$-$C_6)$cycloalkyl, -(4- to 11-membered)heterocycloalkyl, —$(C_6$-$C_{10})$aryl, and -(5- to 11-membered)heteroaryl; and
$X^1$ and $X^2$ are each independently fluoro, chloro or bromo.

2. The process of claim 1, wherein each $R^1$ is independently selected from the group consisting of chloro and —$(C_1$-$C_6)$alkyl, —$O(C_1$-$C_6)$alkyl, and —$(C_3$-$C_6)$cycloalkyl.

3. The process of claim 1, wherein m is 0.

4. The process of claim 1, wherein $R^2$ is selected from the group consisting of chloro, bromo, and iodo.

5. The process of claim 1, wherein $R^2$ is chloro.

6. The process of claim 1, wherein $X^1$ and $X^2$ are the same.

7. The process of claim 1, wherein $X^1$ and $X^2$ are each fluoro.

8. The process of claim 1, wherein m is 0; $R^2$ is selected from the group consisting of chloro and bromo; and $X^1$ and $X^2$ are each fluoro.

9. The process of claim 8, wherein $R^3$ and $R^4$ are both absent.

10. The process of claim 1, wherein m is 0; $R^2$ is selected from the group consisting of chloro and bromo; and $X^1$ and $X^2$ are each chloro.

11. The process of claim 1, wherein m is 0; $R^2$ is selected from the group consisting of chloro and bromo; and $X^1$ and $X^2$ are each bromo.

12. The process according to claim 1, wherein the tertiary alcohol is t-amyl alcohol or t-butyl alcohol.

13. A compound of formula (IVa):

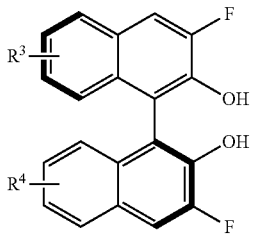

IVa wherein:
R³ and R⁴ are each independently absent or a group selected from the group consisting of halo, —($C_1$-$C_6$)alkyl, —O($C_1$-$C_6$)alkyl, —($C_3$-$C_6$)cycloalkyl, -(4- to 11-membered)heterocycloalkyl, —($C_6$-$C_{10}$)aryl, and -(5- to 11-membered)heteroaryl.

14. The compound of claim 13, wherein in the compound of formula (IVa), R³ and R⁴ are each absent.

15. A method of making the compound of formula (IVa) of claim 13, the method comprising allowing a compound of formula (IV-3):

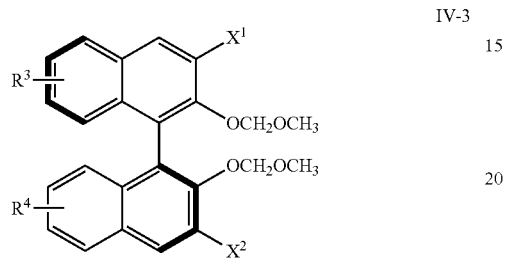

IV-3 to react with a proton source to provide the compound of formula (IVa), wherein
R³ and R⁴ are as defined in claim 13, and
X¹ and X² are each fluoro.

* * * * *